(12) United States Patent
Savoie et al.

(10) Patent No.: US 11,052,190 B2
(45) Date of Patent: Jul. 6, 2021

(54) MEDICAL DEVICE HAVING CAPACITIVE COUPLING COMMUNICATION AND ENERGY HARVESTING

(71) Applicant: Becton, Dickinson and Company, Franklin Lakes, NJ (US)

(72) Inventors: Richard Savoie, Glebe (AU); Gary Searle, Norfolk, MA (US)

(73) Assignee: Becton, Dickinson and Company, Franldin Lakes, NJ (US)

( * ) Notice: Subject to any disclaimer, the term of this patent is extended or adjusted under 35 U.S.C. 154(b) by 479 days.

(21) Appl. No.: 15/686,873

(22) Filed: Aug. 25, 2017

(65) Prior Publication Data

US 2018/0008770 A1    Jan. 11, 2018

Related U.S. Application Data

(62) Division of application No. 14/581,700, filed on Dec. 23, 2014, now Pat. No. 9,764,083, which is a division
(Continued)

(51) Int. Cl.
*A61M 5/142* (2006.01)
*A61M 5/172* (2006.01)
(Continued)

(52) U.S. Cl.
CPC ...... *A61M 5/14248* (2013.01); *A61M 5/1723* (2013.01); *H04B 13/005* (2013.01);
(Continued)

(58) Field of Classification Search
CPC .. A61N 1/3785; A61N 1/378; A61N 1/36014; A61M 5/142
(Continued)

(56) References Cited

U.S. PATENT DOCUMENTS 3,857,382 A    12/1974 Williams, Jr. et al.
3,963,380 A     6/1976 Thomas, Jr. et al.
(Continued)

FOREIGN PATENT DOCUMENTS

EP    0980687 A2    2/2000
EP    1044374 B1   10/2008
(Continued)

OTHER PUBLICATIONS

"Energy Harvesting, Micro Batteries and Power Management ICs: Competitive Environment," Darnell Group, Jun. 11, 2007, <http://www.researchandmarkets.com/reports/655791/energy_harvesting_micro_batteries_and_power>.
(Continued)

*Primary Examiner* — Deanna K Hall
(74) *Attorney, Agent, or Firm* — Dickinson Wright, PLLC

(57) ABSTRACT

Provided is a wearable, self-contained drug infusion or medical device capable of communicating with a host controller or other external devices via a personal area network (PAN). The medical device utilizes a PAN transceiver for communication with other devices in contact with a user's body, such as a physiological sensor or host controller, by propagating a current across the user's body via capacitive coupling. The wearable nature of the medical device and the low power requirements of the PAN communication system enable the medical device to utilize alternative energy harvesting techniques for powering the device. The medical device preferably utilizes thermal, kinetic and other energy harvesting techniques for capturing energy from the user and the environment during normal use of the medical device. A system power distribution unit is provided for managing the harvested energy and selectively supplying power to the medical device during system operation.

3 Claims, 5 Drawing Sheets

Related U.S. Application Data of application No. 12/458,807, filed on Jul. 23, 2009, now Pat. No. 8,939,928.

(51) Int. Cl.
  *H04B 13/00* (2006.01)
  *A61B 5/00* (2006.01)
  *A61B 5/145* (2006.01)

(52) U.S. Cl.
  CPC ......... *A61B 5/0031* (2013.01); *A61B 5/14532* (2013.01); *A61B 2560/0214* (2013.01); *A61M 2205/3538* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/50* (2013.01); *A61M 2205/52* (2013.01); *A61M 2205/825* (2013.01); *A61M 2205/8206* (2013.01); *A61M 2205/8212* (2013.01); *A61M 2205/8237* (2013.01); *A61M 2205/8243* (2013.01); *A61M 2205/8256* (2013.01); *A61M 2209/01* (2013.01); *A61M 2230/201* (2013.01); *A61M 2230/63* (2013.01)

(58) Field of Classification Search
  USPC .................................................... 607/16, 35
  See application file for complete search history.

(56) References Cited

U.S. PATENT DOCUMENTS

| | | |
|---|---|---|
| 4,204,538 A | 5/1980 | Cannon |
| 4,723,947 A | 2/1988 | Konopka |
| 4,755,173 A | 7/1988 | Konopka et al. |
| 5,176,662 A | 1/1993 | Bartholomew et al. |
| 5,226,899 A | 7/1993 | Lee et al. |
| 5,257,980 A | 11/1993 | Van Antwerp et al. |
| 5,453,099 A | 9/1995 | Lee et al. |
| 5,522,803 A | 6/1996 | Teissen-Simony |
| 5,536,249 A | 7/1996 | Castellano et al. |
| 5,545,143 A | 8/1996 | Fischell |
| 5,545,152 A | 8/1996 | Funderburk et al. |
| 5,593,390 A | 1/1997 | Castellano et al. |
| 5,728,074 A | 3/1998 | Castellano et al. |
| 5,820,602 A | 10/1998 | Kovelman et al. |
| 5,851,197 A | 12/1998 | Marano et al. |
| 5,858,001 A | 1/1999 | Tsals et al. |
| 5,858,005 A | 1/1999 | Kriesel |
| 5,925,021 A | 7/1999 | Castellano et al. |
| 5,957,895 A | 9/1999 | Sage et al. |
| 5,968,011 A | 10/1999 | Larsen et al. |
| 5,980,506 A | 11/1999 | Mathiasen |
| 6,017,328 A | 1/2000 | Fischell et al. |
| 6,056,718 A | 5/2000 | Funderburk et al. |
| 6,068,615 A | 5/2000 | Brown et al. |
| 6,074,369 A | 6/2000 | Sage et al. |
| 6,086,575 A | 7/2000 | Mejslov |
| 6,093,172 A | 7/2000 | Funderburk et al. |
| 6,104,913 A | 8/2000 | McAllister |
| 6,110,148 A | 8/2000 | Brown et al. |
| 6,115,636 A | 9/2000 | Ryan |
| 6,123,690 A | 9/2000 | Mejslov |
| 6,175,752 B1 | 1/2001 | Say et al. |
| 6,254,586 B1 | 7/2001 | Mann et al. |
| 6,272,364 B1 | 8/2001 | Kurnik |
| 6,275,717 B1 | 8/2001 | Gross et al. |
| 6,277,627 B1 | 8/2001 | Hellinga |
| 6,293,925 B1 | 9/2001 | Safabash et al. |
| 6,302,866 B1 | 10/2001 | Marggi |
| 6,352,523 B1 | 3/2002 | Brown et al. |
| 6,355,021 B1 | 3/2002 | Nielsen et al. |
| 6,391,005 B1 | 5/2002 | Lum et al. |
| 6,485,461 B1 | 11/2002 | Mason et al. |
| 6,520,938 B1 | 2/2003 | Funderburk et al. |
| 6,521,446 B2 | 2/2003 | Hellinga |
| 6,544,212 B2 | 4/2003 | Galley et al. |
| 6,546,269 B1 | 4/2003 | Kurnik |
| 6,551,276 B1 | 4/2003 | Mann et al. |
| 6,558,351 B1 | 5/2003 | Steil et al. |
| 6,565,509 B1 | 5/2003 | Say et al. |
| 6,576,430 B1 | 6/2003 | Hsieh et al. |
| 6,579,267 B2 | 6/2003 | Lynch et al. |
| 6,589,229 B1 | 7/2003 | Connelly et al. |
| 6,607,509 B2 | 8/2003 | Bobroff et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,692,457 B2 | 2/2004 | Flaherty |
| 6,699,218 B2 | 3/2004 | Flaherty et al. |
| 6,706,159 B2 | 3/2004 | Moerman et al. |
| 6,723,072 B2 | 4/2004 | Flaherty et al. |
| 6,740,059 B2 | 5/2004 | Flaherty |
| 6,749,560 B1 | 6/2004 | Konstrorum et al. |
| 6,749,587 B2 | 6/2004 | Flaherty |
| 6,754,472 B1 | 6/2004 | Williams et al. |
| 6,768,425 B2 | 7/2004 | Flaherty et al. |
| 6,830,558 B2 | 12/2004 | Flaherty et al. |
| 6,830,562 B2 | 12/2004 | Mogensen et al. |
| 6,840,922 B2 | 1/2005 | Nielsen et al. |
| 6,852,104 B2 | 2/2005 | Blomquist |
| 6,949,084 B2 | 9/2005 | Marggi et al. |
| 6,960,162 B2 | 11/2005 | Saadat et al. |
| 6,960,192 B1 | 11/2005 | Flaherty et al. |
| 6,977,180 B2 | 12/2005 | Hellinga et al. |
| 6,997,907 B2 | 2/2006 | Safabash et al. |
| 7,004,928 B2 | 2/2006 | Aceti et al. |
| 7,018,360 B2 | 3/2006 | Flaherty et al. |
| 7,029,455 B2 | 4/2006 | Flaherty |
| 7,052,251 B2 | 5/2006 | Nason et al. |
| 7,064,103 B2 | 6/2006 | Pitner et al. |
| 7,070,580 B2 | 7/2006 | Nielsen |
| 7,083,597 B2 | 8/2006 | Lynch et al. |
| 7,109,878 B2 | 9/2006 | Mann et al. |
| 7,128,727 B2 | 10/2006 | Flaherty et al. |
| 7,137,964 B2 | 11/2006 | Flaherty |
| 7,144,384 B2 | 12/2006 | Gorman et al. |
| 7,207,974 B2 | 4/2007 | Safabash et al. |
| 7,214,207 B2 | 5/2007 | Lynch et al. |
| 7,226,278 B2 | 6/2007 | Nason et al. |
| 7,241,266 B2 | 7/2007 | Zhou et al. |
| 7,303,543 B1 | 12/2007 | Maule et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,329,239 B2 | 2/2008 | Safabash et al. |
| 7,354,420 B2 | 4/2008 | Steil et al. |
| 7,496,392 B2 | 2/2009 | Alarcon et al. |
| 7,981,085 B2 | 7/2011 | Ethelfeld |
| 7,985,199 B2 | 7/2011 | Kornerup et al. |
| 7,985,203 B2 | 7/2011 | Haueter et al. |
| 2002/0040208 A1 | 4/2002 | Flaherty et al. |
| 2003/0014091 A1 | 1/2003 | Rastegar et al. |
| 2003/0055380 A1 | 3/2003 | Flaherty |
| 2003/0109829 A1 | 6/2003 | Mogensen et al. |
| 2003/0176852 A1 | 9/2003 | Lynch et al. |
| 2003/0199823 A1 | 10/2003 | Bobroff et al. |
| 2004/0002682 A1 | 1/2004 | Kovelman et al. |
| 2004/0010207 A1 | 1/2004 | Flaherty et al. |
| 2004/0059316 A1 | 3/2004 | Smedegaard |
| 2004/0078028 A1 | 4/2004 | Flaherty et al. |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0204673 A1 | 10/2004 | Flaherty |
| 2004/0204687 A1 | 10/2004 | Mogensen et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0043687 A1 | 2/2005 | Mogensen et al. |

(56) References Cited

U.S. PATENT DOCUMENTS

| | | |
|---|---|---|
| 2005/0065760 A1 | 3/2005 | Murtfeldt et al. |
| 2005/0090784 A1 | 4/2005 | Nielsen et al. |
| 2005/0101932 A1 | 5/2005 | Cote et al. |
| 2005/0101933 A1 | 5/2005 | Marrs et al. |
| 2005/0113761 A1 | 5/2005 | Faust et al. |
| 2005/0124936 A1 | 6/2005 | Mogensen et al. |
| 2005/0171512 A1 | 8/2005 | Flaherty |
| 2005/0182366 A1 | 8/2005 | Vogt et al. |
| 2005/0215982 A1 | 9/2005 | Malave et al. |
| 2005/0222645 A1 | 10/2005 | Malave et al. |
| 2005/0238507 A1 | 10/2005 | Dilanni et al. |
| 2005/0245799 A1 | 11/2005 | Brauker et al. |
| 2005/0273076 A1 | 12/2005 | Beasley et al. |
| 2005/0283144 A1 | 12/2005 | Shiono et al. |
| 2006/0041229 A1 | 2/2006 | Garibotto et al. |
| 2006/0074381 A1 | 4/2006 | Malave et al. |
| 2006/0129090 A1 | 6/2006 | Moberg et al. |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0200073 A1 | 9/2006 | Radmer et al. |
| 2006/0263839 A1 | 11/2006 | Ward et al. |
| 2006/0264835 A1 | 11/2006 | Nielsen et al. |
| 2006/0281435 A1 | 12/2006 | Shearer et al. |
| 2006/0282290 A1 | 12/2006 | Flaherty et al. |
| 2006/0283465 A1* | 12/2006 | Nickel .................. A61B 5/076 128/898 |
| 2007/0016149 A1 | 1/2007 | Hunn et al. |
| 2007/0021733 A1 | 1/2007 | Hansen et al. |
| 2007/0049865 A1 | 3/2007 | Radmer et al. |
| 2007/0073229 A1 | 3/2007 | Gorman et al. |
| 2007/0073559 A1 | 3/2007 | Stangel |
| 2007/0106199 A1 | 5/2007 | Krivoy et al. |
| 2007/0118405 A1 | 5/2007 | Campbell et al. |
| 2007/0191702 A1 | 8/2007 | Yodfat et al. |
| 2008/0004904 A1 | 1/2008 | Tran |
| 2008/0046038 A1 | 2/2008 | Hill et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0058772 A1 | 3/2008 | Robertson et al. |
| 2008/0071328 A1 | 3/2008 | Haubrich et al. |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0116647 A1 | 5/2008 | Anderson et al. |
| 2008/0119707 A1 | 5/2008 | Stafford |
| 2008/0132842 A1 | 6/2008 | Flaherty |
| 2008/0132881 A1 | 6/2008 | Wood et al. |
| 2008/0147041 A1 | 6/2008 | Kristensen |
| 2008/0160492 A1 | 7/2008 | Campbell et al. |
| 2008/0194924 A1 | 8/2008 | Valk et al. |
| 2008/0215006 A1 | 9/2008 | Thorkild |
| 2008/0261255 A1 | 10/2008 | Tolosa et al. |
| 2008/0264261 A1 | 10/2008 | Kavazov et al. |
| 2008/0269680 A1 | 10/2008 | Ibranyan et al. |
| 2008/0269713 A1 | 10/2008 | Kavazov |
| 2008/0294019 A1* | 11/2008 | Tran .................. A61B 5/04005 600/301 |
| 2008/0294028 A1 | 11/2008 | Brown |
| 2008/0306434 A1 | 12/2008 | Dobbles et al. |
| 2008/0312608 A1 | 12/2008 | Christoffersen et al. |
| 2009/0005724 A1 | 1/2009 | Regittnig et al. |
| 2009/0005728 A1 | 1/2009 | Weinert et al. |
| 2009/0012472 A1 | 1/2009 | Ahm et al. |
| 2009/0076453 A1 | 3/2009 | Mejlhede et al. |
| 2009/0112178 A1 | 4/2009 | Behzadi |
| 2009/0118594 A1 | 5/2009 | Zdeblick |
| 2009/0163965 A1 | 6/2009 | Boyden |
| 2010/0222847 A1 | 9/2010 | Goetz |

FOREIGN PATENT DOCUMENTS

| | | |
|---|---|---|
| JP | 2002-126092 | 5/2002 |
| JP | 2003-520111 | 7/2003 |
| JP | 2003-339137 | 11/2003 |
| JP | 2005-509499 | 4/2005 |
| JP | 2005-535392 | 11/2005 |
| JP | 2007-509652 | 4/2007 |
| JP | 2008-161641 | 7/2008 |
| JP | 2008535548 | 9/2008 |
| WO | WO2007051139 | 5/2007 |
| WO | WO2008008281 A2 | 1/2008 |
| WO | WO2008117214 | 10/2008 |
| WO | WO2008153769 A1 | 12/2008 |
| WO | WO2009021039 | 2/2009 |
| WO | WO2009021052 | 2/2009 |
| WO | WO2009055204 A1 | 4/2009 |
| WO | WO2009055733 A1 | 4/2009 |

OTHER PUBLICATIONS

"Micropower generation and storage," IMEC, 2007.

"Supercapacitors, KSL Series," Cooper Bussmann, St. Louis, 2009, <http://www.cooperbussmann.com/pdf/e81bf50c-96fb-42bb-ab61-733bb80e3a50.pdf>.

Allan, Roger, "The Pulse Quickens for Cutting-Edge Medical Electronics Advances," Electronic Design, Feb. 12, 2009.

Gupta, Puneet, "Personal Area Networks: Say It and You Are Connected," Wireless Developer Network, 2009.

Hammerschmidt, Christoph, "Startup Launches RFID Alternative," EE Times, Aug. 3, 2004.

IDENT Technology AG, Wessling, Germany.

Li, Q. et al., "Biomechanical energy harvesting: Apparatus and method.", IEEE International Conferences on Robotics and Automation 2008, May 19-23, 2008.

Raju, Murugavel, "Energy Harvesting ULP meets energy harvesting: A game-changing combination for design engineers," Texas Instruments, 2008, <http://www.ti.com/corp/docs/landing/cc430/graphics/slyy018_20081031.pdf>.

Seaman; Matthew, "Powering an MSP430 From a Single Battery Cell," Application Report, SLAA398, Sep. 2008, Texas Instruments, <http://focus.ti.com/lit/an/slaa398/slaa398.pdf>.

Thermo Life Energy Corp, "Thermolife Whitepaper," 2008.

* cited by examiner

MEDICAL DEVICE HAVING CAPACITIVE COUPLING COMMUNICATION AND ENERGY HARVESTING

RELATED APPLICATIONS

This application is a divisional of U.S. patent application Ser. No. 14/581,700, filed on Dec. 23, 2014, which is a divisional of U.S. patent application Ser. No. 12/458,807, filed on Jul. 23, 2009 (now U.S. Pat. No. 8,939,928), which is hereby incorporated by reference in its entirety.

FIELD OF THE INVENTION

The present invention relates generally to wearable, self-contained drug infusion devices that take advantage of the wearable nature of such devices to provide lower cost power components and communication components with lower power requirements and enhanced security as compared to wireless communication schemes.

BACKGROUND OF THE INVENTION

Diabetes is a group of diseases marked by high levels of blood glucose resulting from defects in insulin production, insulin action, or both. There are 23.6 million people in the United States, or 8% of the population, who have diabetes. The total prevalence of diabetes has increased 13.5% since the 2005-2007 time period. Diabetes can lead to serious complications and premature death, but there are well-known products available for people with diabetes to help control the disease and lower the risk of complications.

Treatment options for people with diabetes include specialized diets, oral medications and/or insulin therapy. The primary goal for diabetes treatment is to control the patient's blood glucose (sugar) level in order to increase the chances of a complication-free life. It is not always easy, however, to achieve good diabetes management, while balancing other life demands and circumstances.

Currently, there are two principal modes of daily insulin therapy. The first mode includes syringes and insulin pens that require a needle stick at each injection, typically three to four times per day, but are simple to use and relatively low in cost. Another widely adopted and effective method of treatment for managing diabetes is the use of a conventional insulin pump. Insulin pumps can help the user keep their blood glucose levels within target ranges based on their individual needs, by continuous infusion of insulin. By using an insulin pump, the user can match their insulin therapy to their lifestyle, rather than matching their lifestyle to how an insulin injection, for example, is working for them.

Conventional insulin pumps are capable of delivering rapid or short-acting insulin 24 hours a day through a catheter placed under the skin. Insulin doses are typically administered at a basal rate and in a bolus dose. Basal insulin is delivered continuously over 24 hours, and strives to keep one's blood glucose levels in a consistent range between meals and overnight. Some insulin pumps are capable of programming the basal rate of insulin to vary according to the different times of the day and night. Bolus doses are typically administered when the user takes a meal, and generally provide a single additional insulin injection to balance the carbohydrates consumed. Some conventional insulin pumps enable the user to program the volume of the bolus dose in accordance with the size or type of the meal consumed. Conventional insulin pumps also enable a user to take in a correctional or supplemental bolus of insulin to better control their blood glucose level to within their target range.

There are many advantages of conventional insulin pumps over other methods of diabetes treatment. Insulin pumps deliver insulin over time rather than in single injections and thus typically result in fewer large swings in one's blood glucose levels. Conventional insulin pumps reduce the number of needle sticks which the patient must endure, and make diabetes management easier and more effective for the user, thus considerably enhancing the quality of the user's life. Insulin pumps however can be cumbersome to use and are typically more expensive than other methods of treatment. From a lifestyle standpoint, the conventional pump, tubing, and injection set are inconvenient and bothersome for the user.

New advances in insulin therapy provide "wearable" drug infusion devices that are lower in cost and more convenient and comfortable to use than conventional insulin pumps. Some of these devices are intended to be partially or entirely disposable, and in theory provide many of the advantages of conventional insulin pumps without the initial high cost and inconvenience of conventional insulin pumps.

Wearable medical devices capable of performing similar functions as conventional insulin pumps are becoming increasingly more prevalent, but are still high in cost. Such medical devices are typically disposed of after a maximum of 3 days in operation. Driving factors for the duration of use for such medical devices include the viability of the injection site for a prolonged period and the limitations of the power supply in providing the necessary power over this period. Since common wearable medical devices are typically used for such short durations, it is necessary that the unit cost of each medical device be affordably low. In order to realize precise control over a user's insulin rate, typical wearable devices are required to communicate with a host device such as a Blood Glucose Monitor or a Personal Diabetes Monitor. Available wearable devices typically communicate with the host device using well-known wireless technology such as Bluetooth® or ZigBee®. Wireless communication technologies provide effective communication between the wearable device and a host device. However, the components necessary for realizing these technologies are relatively expensive, especially in an application using a disposable medical device. Not only do wireless communication technology components drive up the cost for providing the device, but they also consume sufficient power to shorten the life of the medical device, further driving up cost.

As indicated above, one major constraint of common wearable medical devices is the high cost of providing a reliable power supply for powering the necessary components to realize an effective and fully functional medical device. Further, there must be a balance in realizing a fully functional, affordable medical device and providing the medical device in a package that is convenient, comfortable and discreet for the user. Typical medical devices use a battery or battery array for providing power to the medical device. Such standard arrangements, however, unnecessarily drive up the cost of each medical device and can be bulky and relatively heavy. Further, the standard battery or battery array is usually disposed of at the same time as that of the used wearable medical device, thus contributing to unnecessary waste. Not until the cost of such medical devices is significantly reduced, will wearable medical devices be a viable option for many users.

Accordingly, there is a need in the art for providing more cost-effective wearable medical devices, so that many more diabetes patients can benefit from the advantages these devices provide.

SUMMARY OF THE INVENTION

Exemplary embodiments of the present invention address at least the above problems and/or disadvantages and provide at least the advantages described below. Accordingly, it is an object of exemplary embodiments of the present invention to provide lower power system components and an alternative energy source for powering the medical device that are lower in cost and capable of providing improved functionality and extended life of the wearable medical device. It is a further object of exemplary embodiments of the present invention to provide a device capable of communicating with a host controller and/or body sensor without the added component cost and power drain associated with wireless transceivers while also providing greater security over that of wireless transceivers.

According to one aspect of the present invention, a wearable medical device is provided in contact with a user's body for administering drug therapy to the user, the medical device comprising a microcontroller electrically coupled to a pump mechanism, a transceiver and a power supply system. The microcontroller commands the pump mechanism to administer a drug to the user. The transceiver communicates with a host device on or near the user's body via a personal area network (PAN) that transmits data across the user's body, wherein said host device monitors or controls the medical device. The power supply system selectively provides power to the microcontroller, pump mechanism and transceiver supplied from an energy harvesting component that harvests energy from the user's body. The personal area network transceiver communicates to the host device via an electric field generated on the user's skin at a contact site of the medical device on the user's body. The energy harvesting component stores energy realized by a thermal difference between the user's body and an external environment when the medical device contacts the user's body. The energy harvesting component may also store energy generated by the user's movement when the medical device is positioned on the user's body. The energy harvesting component provides at least a portion of the medical device's energy requirement. The medical device may further comprise an additional power source for providing at least a portion of power to the pump mechanism when actively administering a drug to the user in an active mode, wherein said energy harvesting component powers the medical device when in a lower power state such as a standby mode. The transceiver further communicates with a sensor implantable in the user's body, or in otherwise continuous contact with the user's body, via the personal area network. An embodiment also comprises a sensor electrically coupled to the microcontroller which is an ultra-low power microcontroller.

According to another aspect of the present invention, a medical device is provided in contact with a user's body for administering drug therapy to the user. The medical device comprises a housing in contact with a user's body. The housing further contains a microcontroller controlling a pump mechanism to deliver a drug at a contact site on the user's body. A power supply system comprising an energy harvesting component to harvest energy from the user's body is also provided. A harvested energy storage unit stores the harvested energy, and a power distribution unit selectively provides the stored energy to the microcontroller and the pump mechanism. The power distribution unit preferably provides a first power to the microcontroller when in an active mode, and supplies a second, lower power to the microcontroller in a standby mode of the medical device. The harvested energy storage unit provides at least a portion of the second power and the power supply system further comprises a battery to supply at least a portion of the first power. The housing may further contain a transceiver to communicate with a host monitoring device and a sensor in contact with the user's body via a personal area network that transmits data across the user's body.

A third aspect of the present invention provides a wearable medical device system for providing drug therapy to a user. The system comprises a wearable medical device provided in contact with the user's skin, said medical device comprising a pump mechanism for administering a prescribed volume of a liquid drug to the user. A bodily function sensor is provided in continuous contact with the user's body, and further in communication with the wearable medical device. The wearable medical device further comprises a microcontroller to control the prescribed volume of the drug according to physiological data received from the sensor, wherein the wearable patch pump and the sensor are at least partially powered by energy harvested from the user's body. The sensor may be contained in the wearable patch pump or when implanted in the user's body, the sensor communicates with the wearable patch pump via a personal area network that uses the user's body as a transmission medium to transmit the physiological data.

It is an object of another exemplary embodiment of the present invention to provide a method for administering drug therapy to a user through a wearable medical device in contact with a user's body. The method provides a microcontroller electrically coupled to a pump mechanism, a transceiver and a power supply system. The method configures the microcontroller to command the pump mechanism to administer a drug to the user and harvests energy from the user's body. The method configures the power supply system to selectively provide the harvested energy to the microcontroller, pump mechanism and transceiver and communicates with a host device on or near the user's body via a personal area network that transmits data across the user's body via the transceiver, wherein said host device monitors or controls the medical device and transmits data for at least controlling the administering of the drug to the user. Additionally, the method receives at the medical device said data transmitted via the personal area network from the host device and controls the pump mechanism to administer the drug to the user.

Objects, advantages and salient features of the invention will become apparent to those skilled in the art from the following detailed description, which, taken in conjunction with annexed drawings, discloses exemplary embodiments of the invention.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings, in which.

Throughout the drawings, like reference numerals will be understood to refer to like elements, features and structures.

DETAILED DESCRIPTION OF EXEMPLARY EMBODIMENTS

The matters exemplified in this description are provided to assist in a comprehensive understanding of exemplary embodiments of the invention, and are made with reference to the accompanying figures. Accordingly, those of ordinary skill in the art will recognize that various changes and modifications of the exemplary embodiments described herein can be made without departing from the scope and spirit of the claimed invention. Also, descriptions of well-known functions and constructions are omitted for clarity and conciseness.

Figure 1:
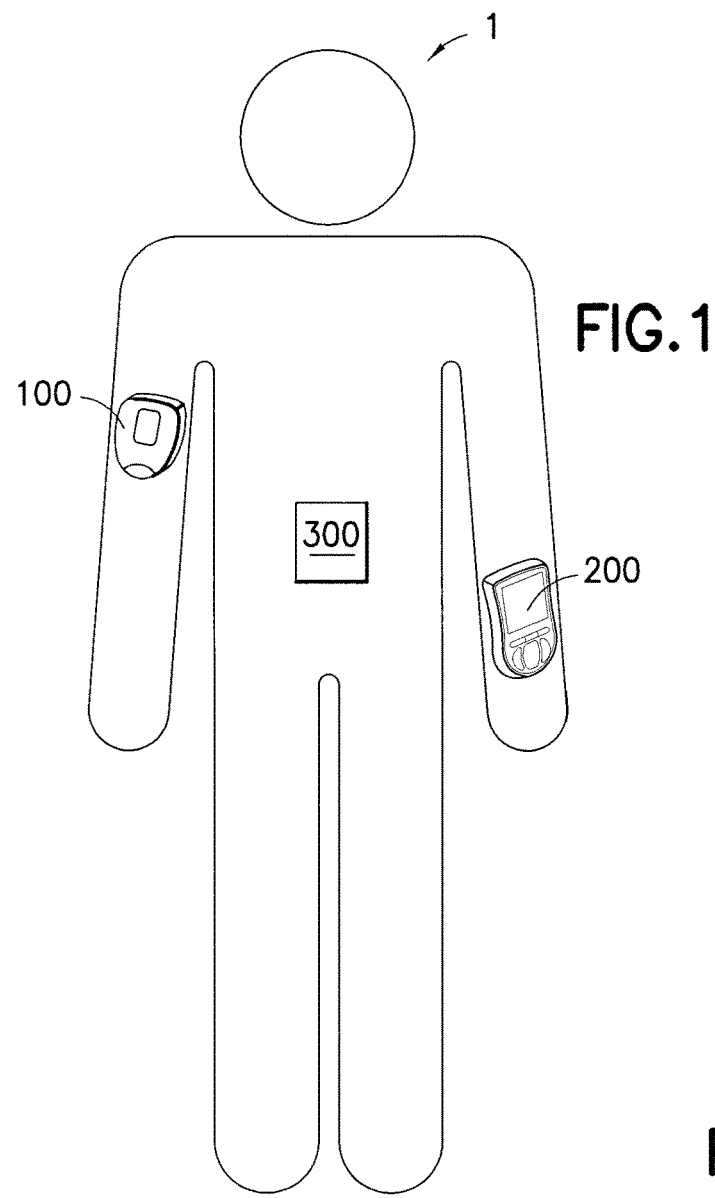
FIG. 1 is an illustration depicting an application of a medical device in accordance with an embodiment of the present invention.
Figure 2:
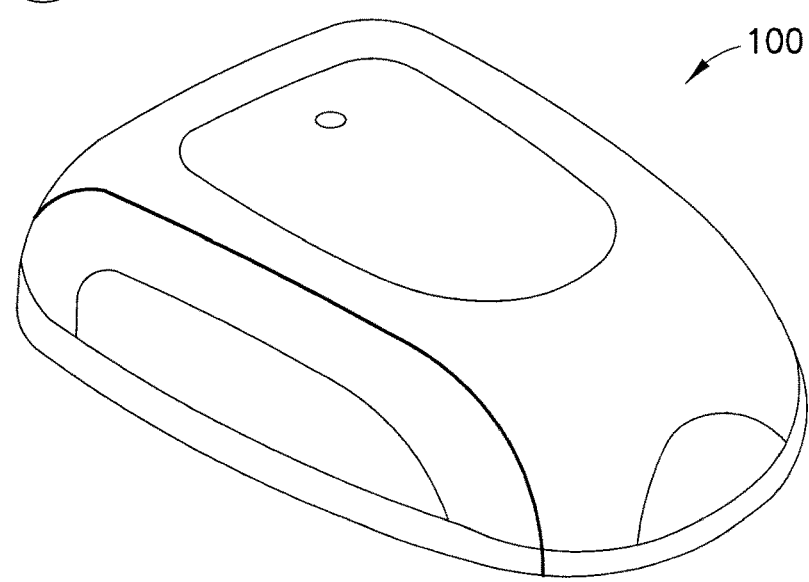
FIG. 2 is an illustration of a medical device in an embodiment of the present invention.

A general embodiment of the wearable medical device 100, constructed in accordance with the present invention is illustrated in FIGS. 1 and 2. Medical device 100 may be used for the delivery of medication, preferably but not necessarily insulin, by continuous infusion into or through the skin of a patient. The medication may be provided in liquid, gel or even solid form in some embodiments. The device 100 is intended to be worn on the surface of the skin by the user, with a cannula (hollow needle) penetrating into the user's skin or transcutaneously through the user's skin into the subcutaneous tissue. Device 100 may also provide intradermal, intramuscular and intravenous drug infusion. Its design is preferably such that the flow rate profile of the liquid medication is fully programmable and can be altered throughout the course of a day by the wearer. Alternatively, device 100 may be pre-programmable and comprise basic functionality for users requiring less control. Other specific functions, features and characteristics of the wearable medical device in accordance with the present invention can be found in commonly-assigned U.S. Pat. No. 6,589,229 issued to Robert I Connelly, et al.

As shown in FIG. 1, exemplary embodiments of the present invention preferably include a host device 200 in communication with medical device 100. Host device 200 can be embodied as a Blood Glucose Monitor (BGM), a Personal Diabetes Monitor (PDM), a PDA, a smartphone, or any other handheld or wearable, lightweight computing device. Alternatively, host device 200 comprises a notebook computer or any other computing device capable of communicating with medical device 100. Additionally, host device 200 and medical device 100 are preferably configured to communicate via additional networks to other external devices for transmitting patient data or other records to a healthcare provider, for instance. This method of communication is not required to be the same as the method used for communicating between the host device 200 and medical device 100. Host device 200 is capable of providing system intelligence for the medical device 100. Host device 200 can be configured to process data received from medical device 100 and communicate to the medical device 100 instructions for any necessary adjustments to the user's infusion rate by adjusting the user's basal rate or modifying a bolus dose. Host device 200 is preferably capable of determining and controlling an injection/infusion rate of a bolus and the duration of the bolus injection/infusion for providing optimum therapeutic benefit for the user. Further, host device 200 may be capable of providing an alarm to alert the user that their insulin level approached or crossed an upper or lower insulin threshold or when a user's blood glucose level trend is violated. Additionally, host device 200 is capable of storing data related to a user's infusion rate and schedule history and can be configured to analyze such data for providing useful trends or statistics to realize a more precise infusion rate for the user. Host device 200 may also be configured to receive system diagnostic information from medical device 100 and alert the user if the medical device 100 is not operating properly.

One of ordinary skill in the art will appreciate that medical device 100, shown in FIG. 1, may also be configured to be fully functional so that all of the functions described above with respect to host device 200 can be incorporated therein. For instance, medical device 100 can further comprise a storage component for storing the infusion rate and schedule information of a user to be uploaded at an optional host device 200, or any other external device, via a personal area network or other communication technique at the user's convenience. Medical device 100 may also optionally comprise necessary components for measuring or sensing the blood glucose levels of a patient and making necessary adjustments to the user's infusion rate, and providing an alarm or alert to the user comprising abnormal insulin levels or system diagnostic information.

Figure 3:
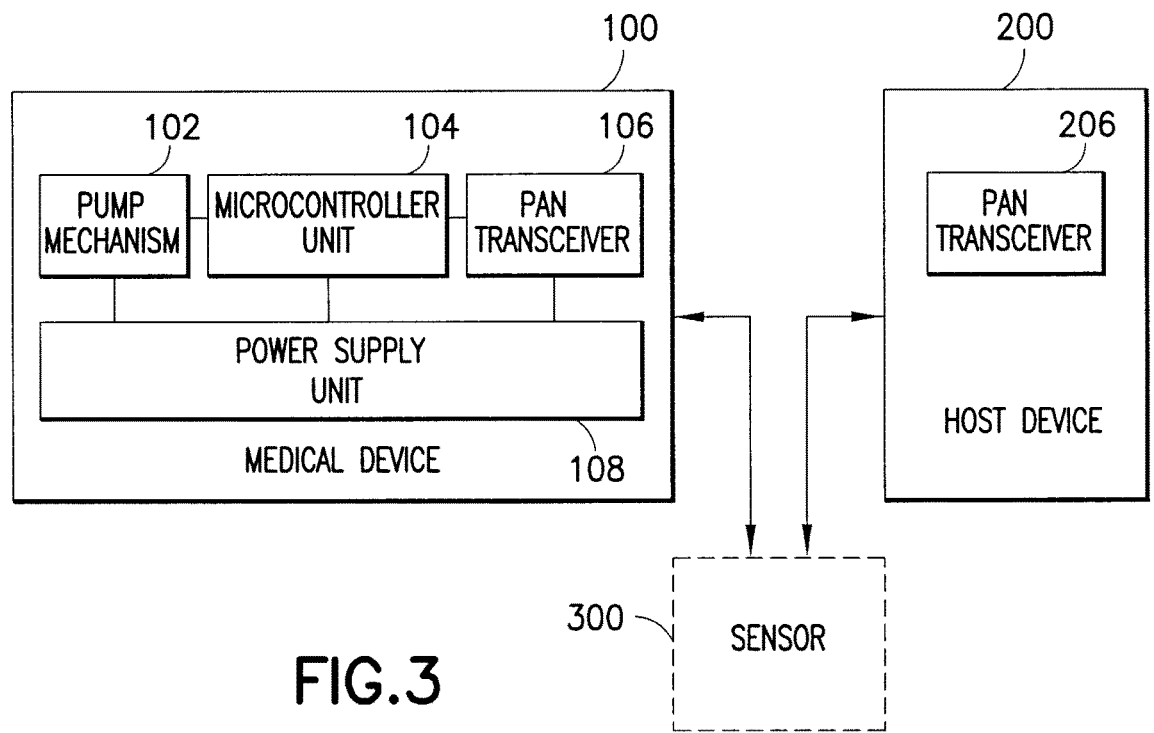
FIG. 3 is a block diagram illustrating the principal components of the medical device in an embodiment of the present invention.

A first exemplary embodiment of medical device 100 in accordance with the present invention is illustrated in FIG. 3. Medical device 100 comprises at least a pump mechanism 102, a microcontroller unit 104, a transceiver system 106 and a power supply system 108. Pump mechanism 102 can be any known mechanism for providing a medicament or drug into or through the user's skin. Pump mechanism 102 minimally provides at least a reservoir or other unit for housing a liquid medicament, a cannula for infusing the medicament into the user, and a pump for actuating the liquid medicament through the cannula. Exemplary embodiments of pump mechanism 102 suitable for use in the present invention can be found in commonly-assigned U.S. Pat. No. 6,589,229 issued to Robert I Connelly, et al. The embodiments disclosed therein are exemplary and are not intended to be limiting. One of ordinary skill in the art will find it reasonable to implement any known pump mechanism suitable in a wearable medical device for dispensing a liquid medicament/drug to a user. It is preferable that pump mechanism 102 be compact, lightweight, accurate and require low power for effective operation.

Microcontroller 104 in the first embodiment of the present invention is provided at least for controlling pump mechanism 102. Microcontroller 104 is preferably an ultra low-power (ULP) programmable controller, ideally operating in a range up to 3.6 V, which combines the necessary processing power and peripheral set to control drug delivery through the pump mechanism 102, monitor an optional sensor 300, and control any communication requirements for communicating with the host device 200. The first exemplary embodiment of the present invention provides a "smart" medical device that is capable of communicating with host device 200 via transceiver system 106. Microcontroller 104 is preferably fully programmable by the host device to precisely control the user's basal infusion rate and necessary bolus injections. Further, host device 200 can control microcontroller 104 to activate pump mechanism 102, perform system diagnostics, monitor system parameters of medical device 100 and record infusion data and other information communicated from medical device 100. Microcontroller 104 in the first embodiment is preferably embodied in a "system on a chip" (SoC) including the circuitry for the transceiver system 106. SoC designs usually consume less power and have a lower cost and higher reliability than the multi-chip systems that they replace. By providing a single chip system, assembly costs may be reduced as well.

Transceiver system 106, provided in medical device 100 in the first embodiment of the present invention, is compatible with the transceiver at the host device 200 and any other peripheral units such as optional bodily function sensor 300 in order to communicate with each device. As discussed above, in a "smart" medical device of the first embodiment, transceiver system 106 is provided for communicating at least system diagnostic data, infusion rate or infusion schedule information to host device 200 or some other external device. Additionally, transceiver system 106 receives commands and data from host device 200 enabling the programming of microcontroller 104 and control of other system functions of medical device 100. Diagnostic data can refer to any information about the functionality of the medical device and its system components, such as whether the cannula is blocked or otherwise rendered unusable, the remaining volume of liquid medicament available, and the remaining power available for controlling the medical device 100.

Conventional "smart" medical devices currently use radio frequency (RF) wireless communications such as Bluetooth®, Zigbee®, 802.11, or other conventional solutions. Some medical devices even communicate with the host device via a line-of-sight using infrared (IR) technology. Wireless communication systems, since they do not require a line of sight, are preferred over IR technology. Conventional wireless technology, however, is a driving contributor in the prohibitive cost of medical devices that use their respective technologies. Conventional wireless systems require an RF transceiver and antenna to operate. Advantageously, exemplary embodiments of the present invention use a capacitively coupled personal area network (PAN) to transceive data between medical device 100 and host device 200 through the user's skin, without the use of antennas. A personal area network, in the exemplary embodiments, can be created with simple, low-cost microcontrollers and analog components, requires less power to operate than RF systems and are at least as secure as RF systems. The use of a personal area network in the exemplary embodiments reduces the overall cost for device/host communications and enables extended use duration due to the reduced component cost and lower power requirements. As previously discussed, an exemplary PAN transceiver system 106 is preferably packaged in a SoC design with microcontroller 104 for further minimizing the overall cost of medical device 100.

Figure 5:
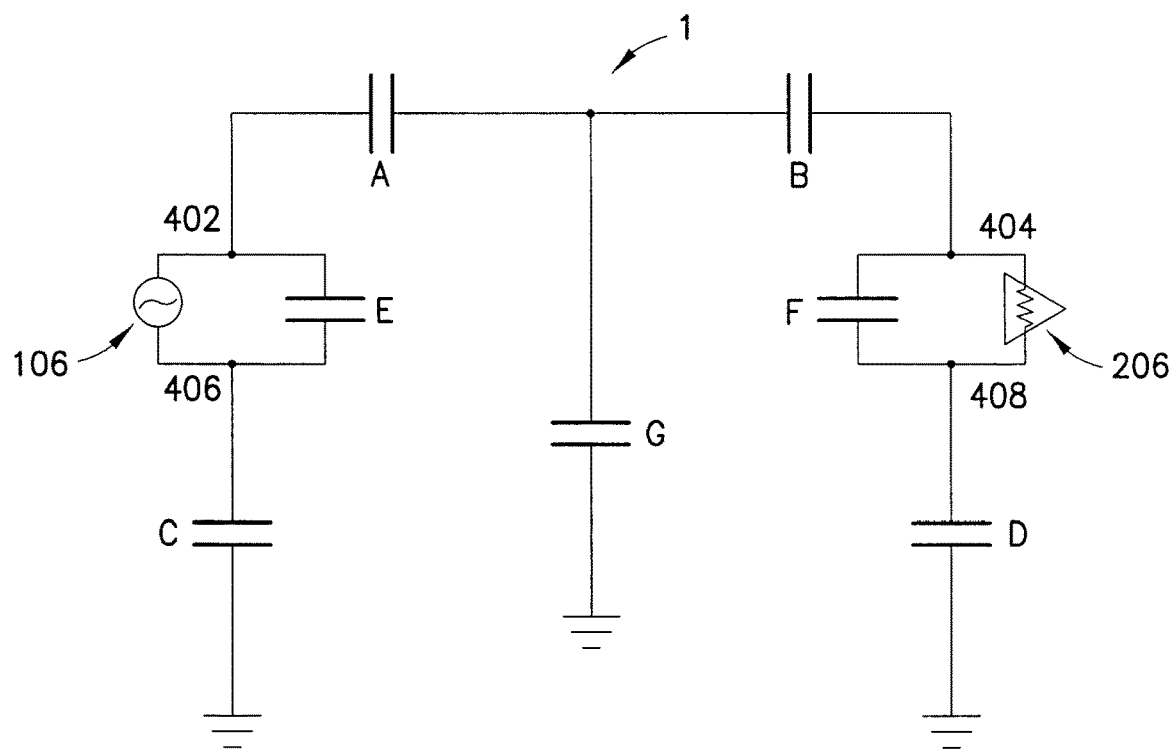
FIG. 5 is an electrical circuit model of the personal area network depicted in FIG. 4.
Figure 4:
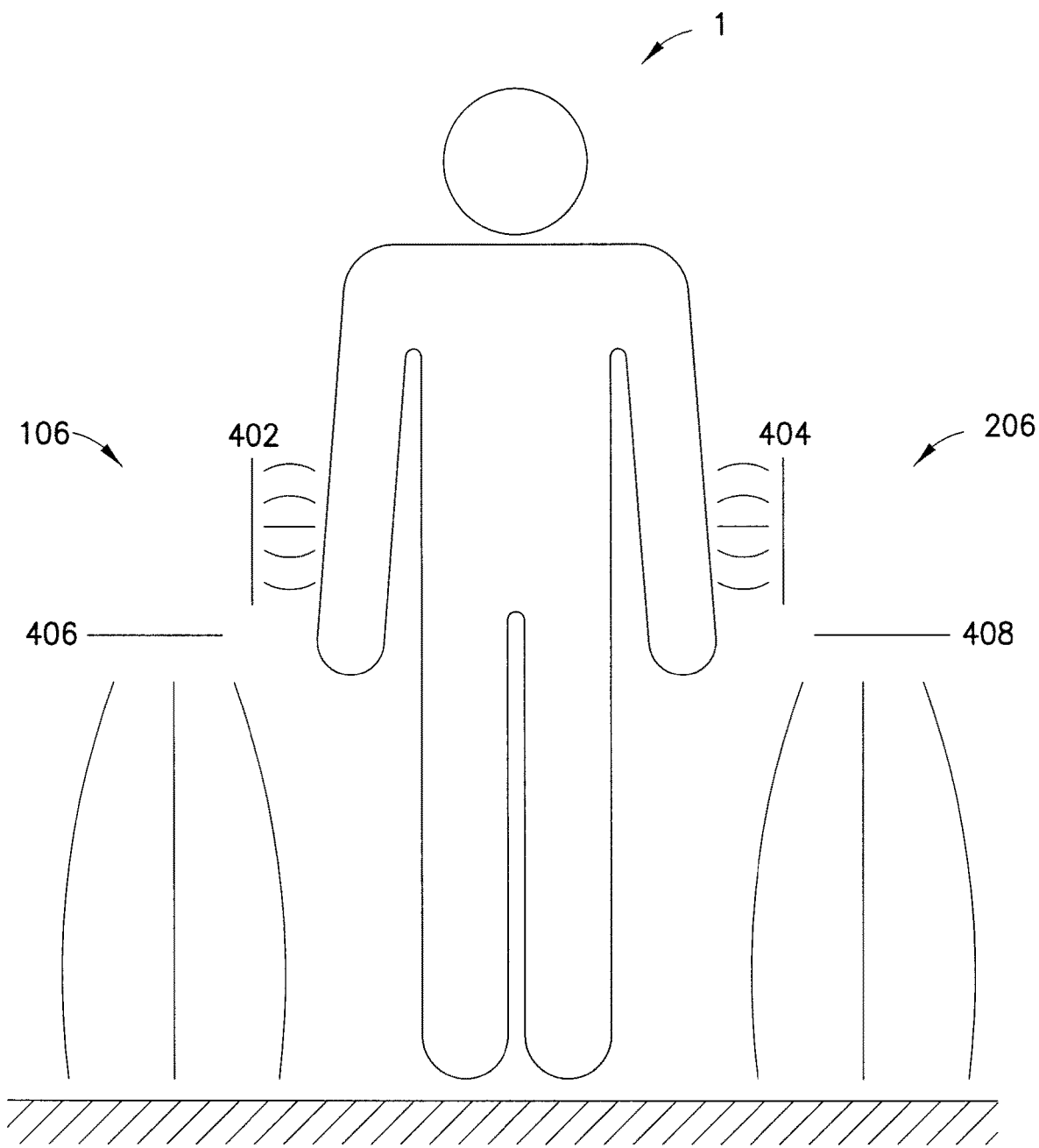
FIG. 4 is an illustration depicting the operation of a personal area network.

PAN transceiver 106 preferably establishes a personal area network to communicate with host device 200 via a "near field" electric field that transmits data using the human body as a transport medium. Medical device 100 and host device 200 each need PAN transceivers 106 and 206, respectively, in order to communicate to each other through the body. In an exemplary personal area network as illustrated in FIGS. 4 and 5, a transmitter electrode 402, facing the body at transceiver 106, and the user's skin act as a capacitor A. In the same manner, the user's skin and a receiver electrode 404, at transceiver 206, act as a capacitor B. As indicated in FIG. 5, PAN transceiver 106, acting as a transmitter, is capacitively coupled to PAN transceiver 206, acting as a receiver. The embodiment shown in FIG. 5 is by example only. In another embodiment, PAN transceiver 206 may act as the transmitter with PAN transceiver 106 being the receiver. The human body acts as a conductor capable of carrying a current through the body from transceiver 106 to transceiver 206. "Earth ground" includes any conductors and dielectrics in the environment in close proximity to the user's body, and acts as a return path. Electrode 406 at transceiver 106 and "earth ground" act as a capacitor C, and electrode 408 at transceiver 206 and "earth ground" act as a capacitor D. Additionally, "earth ground" needs to be electrically isolated from the human body in order to prevent shorting of the communication circuit, thus effectively acting as capacitor G. FIG. 5 illustrates an electric circuit model of a personal area network in an exemplary embodiment of the present invention. Because electrode 402 has a lower impedance to the user's body than electrode 406, the transmitter is enabled to provide an oscillating potential on electrode 406. The oscillating potential results in a displacement current that is real and is transferred to the human body. Transceiver 106 can effectively modulate the displacement current to transmit data across the human body to the receiver. In an exemplary embodiment, transceiver 106 may comprise an encoder/decoder for encoding data received from microcontroller 102 and circuitry for converting the data into a modulated displacement current. Transceiver 206 may comprise an amplifier to amplify a received displacement current, an analog to digital converter for converting the electric current into data and a decoder for decoding the data into bits of information to be processed by the host device 200. The displacement current transmitted across the user's body is very small, thus not only is power consumption reduced, but such a small current ensures that the transmitted signal does not radiate far from the user's body, therefore, providing a distinct security advantage over wireless communication techniques.

The above PAN communication system ensures that only people in direct contact with a user are capable of detecting the signals propagating across the user's body. Alternatively, in conventional wireless technologies, a transmitted signal can be detected by anyone with a receiver in the respective range of the wireless technology. Transmitters and receivers using Bluetooth® can transceive signals in a range from 30 ft. to 100 ft. Thus, PAN communication techniques are inherently more secure. However, additional techniques are desirable for coding and encrypting the transmitted current so that a user's private medical information cannot be detected or deciphered by anyone who comes into contact with the user. Coding techniques for preventing cross-talk between PAN devices is desirable so that a husband and wife, or other acquaintance, using PAN devices can hold or shake hands without influencing the data communication of either user's personal area network. Additionally, the signal transmitted across the user's body can be further encrypted so that any information transmitted by bodily contact will be unintelligible to unauthorized recipients. The specific techniques and methods for coding and encryption are not specific to the present invention. Any high reliability/low error version of a standard multi-user across single channel networking protocol, such as TCP/IP, can be effectively implemented in exemplary embodiments of the present invention. For instance, suitable handshaking techniques/protocols and encryption key management and algorithms for use in exemplary embodiments of the present invention may be similar to those currently used in Bluetooth® and Wi-Fi networks. It would be appreciated by one of ordinary skill in the art, that the particular coding and encryption techniques implemented in the exemplary embodiments of the present invention, while similar to those techniques discussed above, may be provided in a lighter, less complex protocol.

The necessary transceiver components for realizing the functionality of the exemplary personal area network discussed above, are widely available and relatively low in cost. Additionally, transceivers 106 and 206 can be realized in a single integrated circuit or included in the SoC design discussed above, which is even cheaper to produce and will consume even less power.

Analysis of a conventional medical device showed a typical steady state current usage of up to 15 mA while performing RF communications. Since an exemplary personal area network of the present invention transmits data using an ultra-low current signal propagating on the user's skin, data transfer can reasonably be achieved with 30 nA of current. Associated circuitry required to amplify and digitally acquire the data from the received electric signal could require up to 1 mA of additional current, thereby still achieving a factor of 10 reduction in power consumption for communications. Implementation of an exemplary PAN communication system in medical device 100 and host device 200, effectively realizes a significant decrease in power consumption for the device, thus resulting in less expensive, fewer or smaller power components for supplying the power necessary for system operations. A reduction in power requirements achieves an overall reduction in cost for the medical device 100 and reduces the number or size of power components, thus also reducing waste. Further, the low power requirements of the PAN communication system as well as the wearable nature of medical device 100 enable medical device 100 to utilize alternative energy sources for powering the device.

Figure 6:
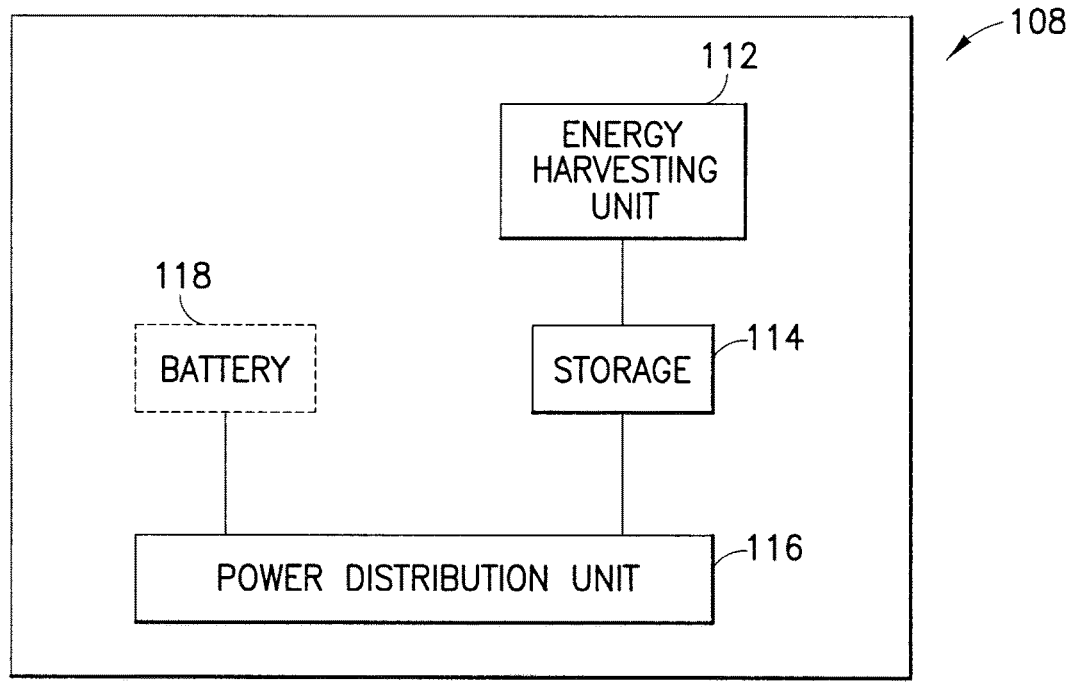
FIG. 6 is a block diagram illustrating the principal components of a power system in an embodiment of the present invention.

FIG. 6 illustrates an exemplary embodiment of power system 108 for supplying necessary power to the pump mechanism 102, microcontroller 104 and PAN transceiver system 106. Power system 108 comprises an energy harvesting unit 112, storage unit 114 and power distribution unit 116. As used herein, the term "harvesting" should be considered synonymous with similar terms such as "scavenging", and refers to the use of any locally available energy source. Energy harvesting unit 112 preferably comprises an energy harvesting circuit that uses either kinetic energy or the Seebeck effect (thermal) to store charge and create voltage for use by the system components of medical device 100. The exemplary embodiments of medical device 100 as a wearable patch pump in contact with the user's skin, lends itself the opportunity for efficient and optimum energy capture from the user's body. Kinetic and thermal energy harvesting techniques are well known, and accordingly, a detailed description of well known aspects of the same is omitted for clarity and conciseness. Kinetic energy harvesting techniques capture energy by reclaiming minute and unnoticeable amounts of energy from natural movement of the device user that can be converted to usable charge for medical device 100. Examples of kinetic energy that can be utilized include vibratory energy and limb deceleration. These embodiments may particularly be preferred when the medical device 100 is worn on the user's arm. Thermal energy harvesting techniques utilize the Seebeck effect to transform a temperature difference between the ambient environment and the patient's skin, where medical device 100 is adhered, into a usable voltage. Temperature differentials between opposite segments of a conducting material result in heat flow and consequently charge flow (current), since mobile, high-energy carriers diffuse from high to low concentration regions. One technique electrically joins thermopiles consisting of n- and p-type materials at the high temperature junction, thereby allowing heat flow to carry the dominant charge carriers of each material to the low temperature end, establishing a voltage difference across base electrodes of the thermopiles in the process.

An exemplary embodiment of power system 108 utilizes a temporary storage circuit or device for storing the harvested charge until it is supplied to power a system component of medical device 100, such as PAN transceiver 106. An exemplary embodiment of the present invention utilizes an ultracapacitor as storage unit 114 to store the harvested energy. Ultracapacitors are advantageous because of their high energy density and quick charging times, thus providing a suitable option for powering the systems of an exemplary medical device 100. It should be appreciated by one of ordinary skill in the art, that storage unit 114 may comprise any temporary storage component, circuitry or technique that is known in the art, and is not particularly limited to an ultracapacitor. Power distribution unit 116, may comprise a power management circuit or other known component for providing the necessary power requirement from power storage unit 114 to each system device.

An exemplary embodiment of power system 108 in medical device 100 preferably comprises a single power source such as energy harvesting component 112, capturing, for instance, thermal or kinetic energy from the user's body and the user's natural movement. In an exemplary embodiment of the present invention comprising ultra low-power microcontroller 104 and low-power PAN transceiver system 106, a single energy harvesting source may be sufficient for providing the complete power requirements for medical device 100. Additionally, a single energy harvesting source may necessarily provide sufficient power for medical device 100 in embodiments that use a preprogrammed microcontroller 104 and do not provide a communications transceiver system. The power supplied to medical device should be sufficient for enabling operation of the medical device in an active mode and a standby mode. In the standby mode, the microcontroller preferably consumes about 10 microamperes of current but no more than 20 microamperes. In the active mode, the microcontroller preferably consumes about 10 milliamperes but no more than 20 milliamperes.

In some embodiments, power system 108 may additionally comprise a battery 118. Battery 118 may comprise any one of well known power storage units, or an array of such units, known in the art including, but not limited to, standard alkaline cells, rechargeable cells and ultracapacitors. In such embodiments, power distribution unit 116 can optimally manage the distribution of power from the battery 118 and the energy harvesting storage unit 114 to provide increased performance and extended life of medical device 100. One embodiment of medical device 100 would use battery 118 for long-term storage power or "off" mode, and in an active mode, such as during a high-discharge time for pump mechanism 102 to dispense a drug to the user. Harvested energy storage unit 114 is then preferably used to supplement the idle/standby mode of medical device 100, which has been shown in some systems to be the highest overall power drain to the system. By utilizing energy harvesting as the sole or partial power source for an exemplary embodiment of medical device 100, the device life could be extended or the battery requirements be reduced, thereby increasing performance and reducing cost in comparison to existing patch pumps.

Figure 7:
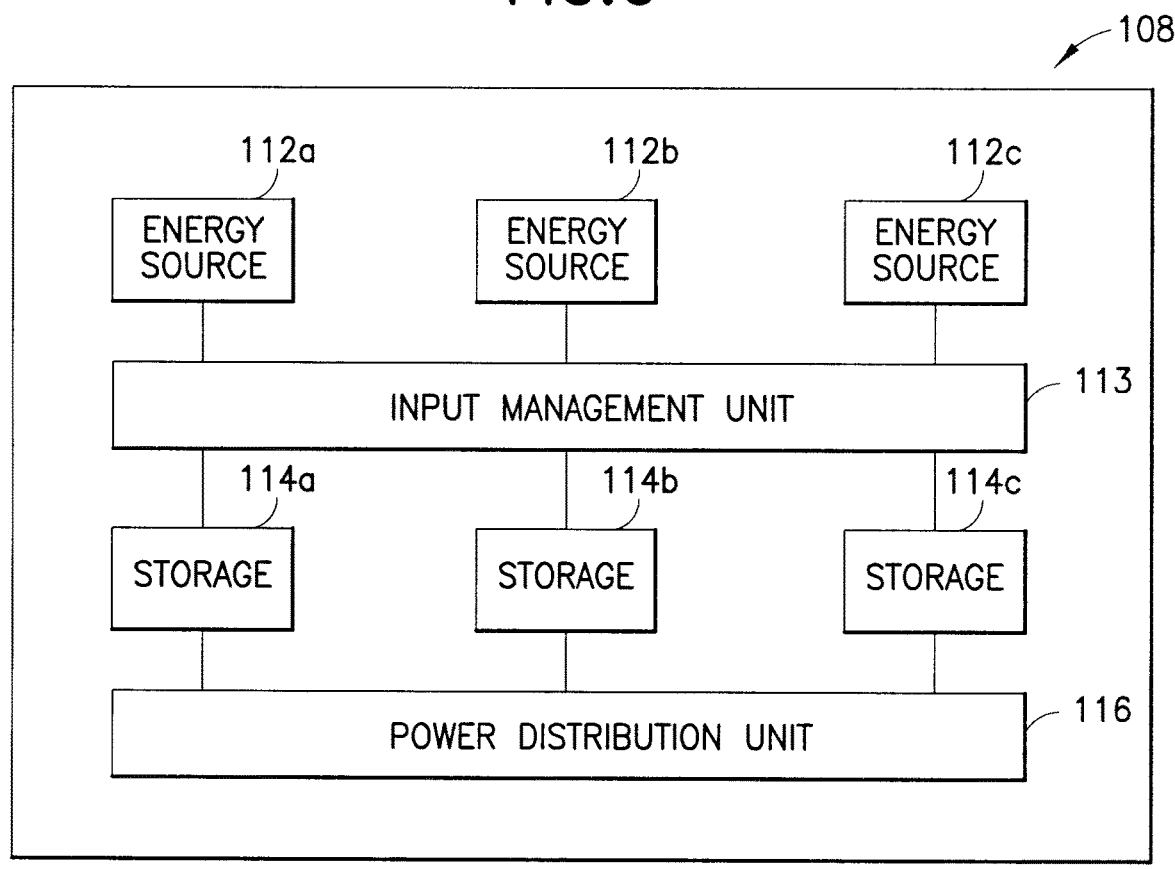
FIG. 7 is a block diagram illustrating an additional embodiment of a power system in accordance with an embodiment of the present invention.

Another embodiment of power system 108 for use in exemplary embodiments of the present invention is illustrated in FIG. 7. In this embodiment, power system 108 comprises a plurality of energy harvesting units 112a, 112b and 112c. Energy harvesting units 112a-c can comprise any combination of kinetic harvesting units, thermal harvesting units and standard power sources such as batteries, as discussed above. Additionally, if the particular embodiment of medical device 100 comprises a transceiver system 106, one of energy harvesting units 112a-c can be provided for harvesting energy from communications received from host device 200 at the transceiver. FIG. 7 illustrates three energy harvesting units by example only. One of ordinary skill in the art would appreciate that power system 108 may comprise any number and combination of energy harvesting units that are suitable for the particular medical device. Additionally, energy harvesting units 112a-c are not limited to harnessing kinetic energy, thermal energy or energy from communications with a host device. Additional systems for harnessing energy from electromagnetic energy, such as from RF energy, or any other sources that are feasible for powering medical device 100 may also be used. RF energy is pervasive in the external environment and may be captured by medical device 100 to directly power the device or provide a supplemental source of power for medical device 100. Exemplary techniques for harnessing RF energy suitable for use in the present invention can be found in U.S. Patent Publication No. 2006/0281435 to John G. Shearer, et al., which is expressly incorporated herein by reference.

In the embodiment illustrated in FIG. 7, input management unit 113 can comprise simple voltage rectifiers and charge pumps for translating the intermittently captured energy from energy harvesting devices 112a-c into a usable voltage for storage in any of storage units 114a-c. Storage units 114a-c may comprise various types of rechargeable batteries, ultracapacitors or other temporary storage devices recognized in the art. One of storage units 114a-c may optionally comprise a single use or disposable battery or battery array as similar described in FIG. 6. System power distribution unit 116 is preferably provided for managing and dividing the available energy from storage units 114a-c amongst the systems in the medical device 100 that require different types of power. For example, system power distribution unit 116 selectively supplies necessary power from a suitable storage unit to pump mechanism 102 that requires short bursts of higher current at a stable voltage to inject a drug into the user, while microcontroller 104 and exemplary PAN transceiver system 106 require smaller currents for optimum functionality. Additionally, system power distribution unit 116 optimally designates an even lower power for powering medical device 100 in an "off" mode for long term storage of the device before it is used. The power system illustrated in FIG. 7 preferably realizes an optimal combination of energy harvesting units and standard power supply units, such as a battery, to provide optimum functionality for medical device 100 and extended life, at minimal cost.

Figure 8:
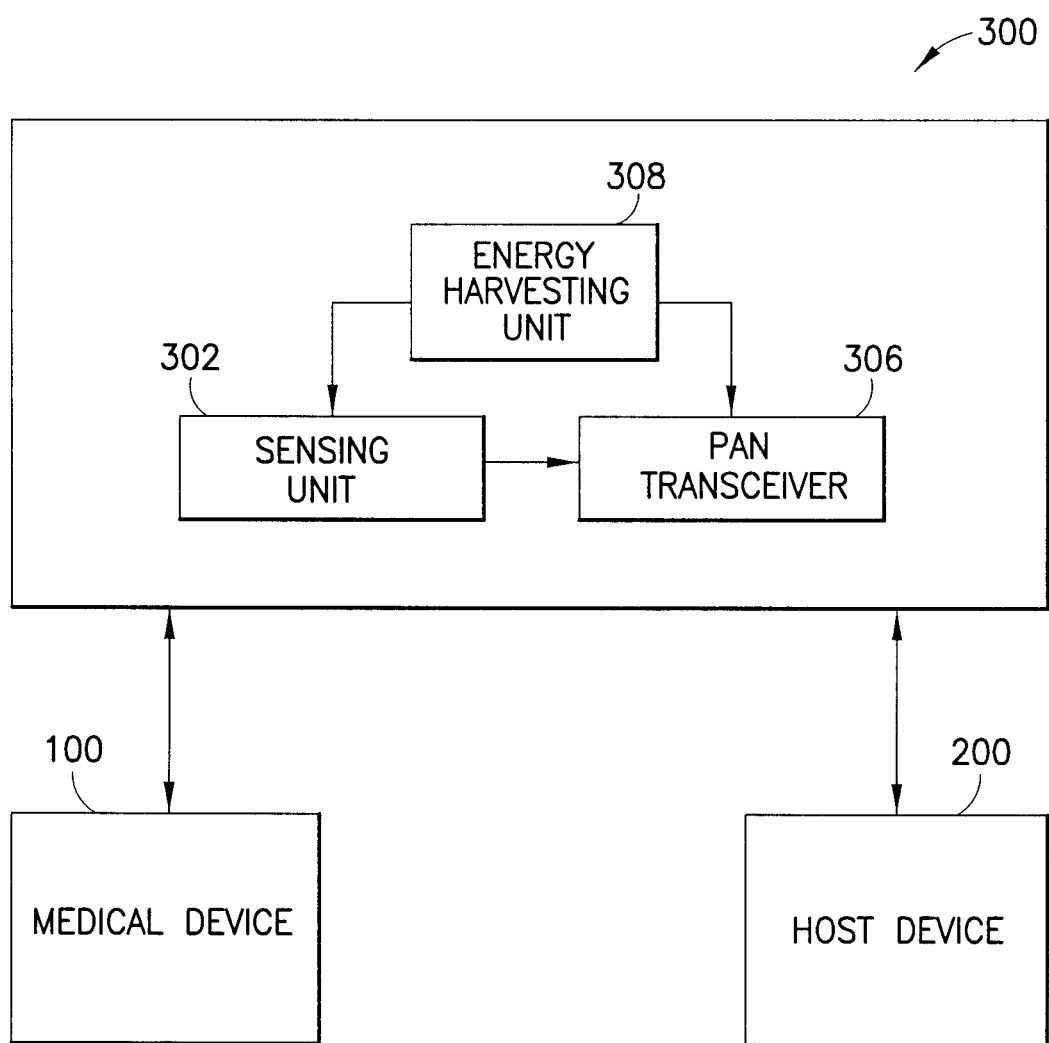
FIG. 8 is a block diagram illustrating the principal components of a sensing unit in accordance with an embodiment of the present invention.

FIG. 8 illustrates an exemplary embodiment of optional bodily function sensor 300 depicted in FIG. 3 for use in conjunction with exemplary embodiments of medical device 100. Specific to diabetes care, the medical industry is migrating toward closed loop systems for insulin infusion. Ideal systems, typically referred to as an "artificial pancreas", would provide "real time" or "near real time" feedback for precise insulin infusion control. Bodily function sensor 300 may be a transcutaneous analyte sensor or biosensor and is preferably a blood glucose sensor that may be provided as part of medical device 100 or inserted at a separate site on the user, and may even be surgically implantable into the user. Sensor 300 may be provided as a temporary or disposable single use sensor or alternatively may be implemented for repeated or consistent use over an extended duration. In embodiments that include sensor 300 in medical device 100, sensor 300 optimally receives power from power system 108 and provides data to transceiver 106 for communication to host device 200. Host device 200 preferably processes any data received through the exemplary personal area network described above and modifies the user's infusion rate, if necessary. Host device may further perform any of the functions described in exemplary embodiments above. FIG. 8 illustrates sensor 300 as an implantable device or otherwise inserted into the user at a site separate from medical device 100. In this exemplary embodiment, sensor 300 further comprises sensing unit 302, energy harvesting unit 308, and PAN transceiver system 306. Energy harvesting unit 308 may comprise any of the above described energy harvesting units and preferably provides the only source of power for the sensor 300. PAN transceiver 306 operates as discussed above to transmit sensing data received from sensing unit 302. PAN transceivers 106 and 206 are capable of receiving any data transmitted from PAN transceiver 306 through the exemplary personal area network described above. An exemplary embodiment of sensor 300, in accordance with the present invention, combines the advantages of the energy harvesting system 308 and PAN transceiver 306 to realize minimum cost and maximum functionality in providing precise insulin infusion control for a user using medical device 100.

One of ordinary skill in the art would appreciate that the features of the above exemplary embodiments may be similarly provided in a number of applications and are not limited to the above disclosure. Any other skin-surface, wearable, implantable and handheld devices can all utilize the above features and techniques for providing a body based personal area network of complex, low-power devices at minimal cost. In addition to the insulin patch pump devices disclosed herein, other non-pump insulin infusion devices for patients of varying needs can be implemented with the above discussed features, such as a programmable insulin pen device or a controller in combination with an insulin absorption patch or electrosensitive gel patch. Additionally, other physiological information such as systolic pressure, heart rate and other metrics can all be monitored and captured via a respective device using the exemplary personal area network. Similarly, implantable defibrillators and other devices can all be controlled from a single master/host device. An exemplary personal area network can theoretically support many more than just two or three devices. Such network can also be used to communicate to any stationary devices when the user makes physical contact with them. One embodiment could provide automated data transmission such as populating patient records stored in a handheld or wearable device when touching a computer fitted with a compatible PAN transceiver. Another embodiment could provide emergency personnel with immediate data concerning a patient's physiological functions just by making skin to skin contact to establish a communications link between compatible devices on each person. As discussed above, each of these embodiments can be implemented in a secure PAN, so as to ensure user privacy and security of sensitive medical information.

While the present invention has been shown and described with reference to particular illustrative embodiments, it is not to be restricted by the exemplary embodiments but only by the appended claims and their equivalents. It is to be appreciated that those skilled in the art can change or modify the exemplary embodiments without departing from the scope and spirit of the present invention.

What is claimed is:

1. A wearable medical device system for providing drug therapy to a user, the system comprising:
   a wearable medical device provided in contact with the user's skin and comprising a transceiver capacitively coupled to the user's skin and utilizing the user's body tissue as a communication medium, said transceiver modulating an electrical potential at an electrode in contact with the user's skin, said medical device comprising a pump mechanism for administering a prescribed volume of a liquid drug to the user; and
   at least one bodily function sensor provided in continuous contact with the user's skin and comprising a transceiver capacitively coupled to the user's skin and utilizing the user's body tissue as a communication medium, the transceiver sensing a modulated electrical potential at an electrode in contact with the user's skin, and further in communication with the wearable medical device via a personal area network formed with the user's body tissue between the wearable medical device transceiver and the bodily function sensor transceiver;
   wherein the wearable medical device further comprises a microcontroller to control the prescribed volume of the drug according to physiological data received from the sensor, wherein the wearable patch pump and the sensor are at least partially powered by energy harvested from the user's body.

2. The medical device system of claim 1, wherein the sensor is contained in the wearable patch pump.

3. The medical device system of claim 1, wherein the sensor is implanted in the user's body and the sensor communicates with the wearable patch pump via a personal area network that uses the user's body as a transmission medium to transmit the physiological data.

* * * * *